(12) United States Patent
Xu

(10) Patent No.: US 9,566,014 B2
(45) Date of Patent: Feb. 14, 2017

(54) SYSTEM FOR CARDIAC MR AND MR CINE IMAGING USING PARALLEL IMAGE PROCESSING

(75) Inventor: Jian Xu, New Hyde Park, NY (US)

(73) Assignee: Siemens Healthcare GmbH, Erlangen (DE)

(*) Notice: Subject to any disclaimer, the term of this patent is extended or adjusted under 35 U.S.C. 154(b) by 0 days.

(21) Appl. No.: 13/467,219

(22) Filed: May 9, 2012

(65) Prior Publication Data
US 2013/0116545 A1 May 9, 2013

Related U.S. Application Data

(60) Provisional application No. 61/557,645, filed on Nov. 9, 2011.

(51) Int. Cl.
A61B 5/055 (2006.01)
A61B 5/0402 (2006.01)
G01R 33/563 (2006.01)
A61B 5/00 (2006.01)
G01R 33/48 (2006.01)
G01R 33/56 (2006.01)
G01R 33/561 (2006.01)
G01R 33/567 (2006.01)

(52) U.S. Cl.
CPC ......... *A61B 5/0402* (2013.01); *A61B 5/0044* (2013.01); *A61B 5/055* (2013.01); *A61B 5/7289* (2013.01); *G01R 33/56325* (2013.01); *A61B 5/0037* (2013.01); *G01R 33/4822* (2013.01); *G01R 33/5602* (2013.01); *G01R 33/5611* (2013.01); *G01R 33/5616* (2013.01); *G01R 33/5673* (2013.01)

(58) Field of Classification Search
USPC ......................................... 600/407, 410–423
See application file for complete search history.

(56) References Cited

U.S. PATENT DOCUMENTS 6,438,403 B1 8/2002 Cline et al.
7,797,031 B1 * 9/2010 Foo ............................. 600/410
(Continued)

OTHER PUBLICATIONS

"SENSE: Sensitivity Encoding for Fast MRI" by K.P. Pruessmann et al. Magnetic Resonance in Medicine. 42:952-962 (1999).*

(Continued)

Primary Examiner — Tse Chen
Assistant Examiner — Jason Ip

(57) ABSTRACT

A system for cardiac MR imaging receives a heart rate signal representing heart electrical activity. The system, over multiple successive heart cycles, uses multiple MR imaging RF coils in gradient echo imaging a patient heart, synchronized with the heart rate signal and uses an inversion recovery pulse for inverting myocardium tissue MR signal for an individual heart cycle, to acquire, within multiple individual successive portions of an individual heart cycle, corresponding successive multiple patient heart images. An individual image of an individual heart cycle portion is derived from multiple heart image representative data sets comprising a reduced set of k-space data elements acquired using corresponding multiple coils of the RF imaging coils. An image generator generates an MR image of an individual heart cycle portion using the multiple heart image representative data sets comprising the reduced set of k-space data elements.

16 Claims, 4 Drawing Sheets

(56) References Cited

U.S. PATENT DOCUMENTS

| | | | |
|---|---|---|---|
| 2003/0171671 A1* | 9/2003 | Miyazaki | 600/420 |
| 2005/0272997 A1* | 12/2005 | Grist et al. | 600/410 |
| 2007/0038073 A1* | 2/2007 | Mistretta | 600/410 |
| 2010/0268066 A1* | 10/2010 | Rehwald et al. | 600/419 |

OTHER PUBLICATIONS

"Sparse MRI: The Application of Compressed Sensing for Rapid MR Imaging" by M. Lustig et al. Magnetic Resonance in Medicine. 58:1182-1195 (2007).*

"Free -breathing 3D stead-State Free Precession Coronary MR Angiography with Radial k-Space Sampling: Comparison with Cartesian k-Space Sampling and Cartesian Gradient-Echo Coronary MR Angiography—Pilot Study" by. E. Spuentrup et al. Radiology. pp. 581-586. 2004.*

Weiger, Markus, et al. "Accelerated cardiac breathhold imaging using coil sensitivity encoding." Proceedings of the ISMRM 6th Annual Meeting, Sydney. 1998.*

Jung, Hong, et al. "Radial k-t FOCUSS for high-resolution cardiac cine MRI." Magnetic Resonance in Medicine 63.1 (2010): 68-78.*

J Xu, "Initial Comparative Evaluation of a Five-Minute Comprehensive Cardiac MR Examination Using Highly Accelerated Parallel Imaging", published in ISMRM 2011.

Peter Kellman, et al., "Phase-Sensitive Inversion Recovery for Detecting Myocardial Infarction Using Gadolinium-Delayed Hyperenhancement", Magnetic Resonance in Medicine, 47:372-383 (2002).

J Xu, "Feasibility of Dynamic 4D Whole Heart Viability Imaging Within a Single Breath-Hold Using Highly Accelerated Parallel Imaging and Compressed Sensing", published in ISMRM 2012.

Armin M Huber, et al., "Phase-Sensitive Inversion-Recovery MR Imaging in the Detection of Myocardial Infraction", Radiology 2005; 237:854-860.

Orlando P Simonetti, et al., "An Improved MR Imaging Technique for the Visualization of Myocardial Infarction", Radiology 2001; 218:215-223.

Ricardo Otazo, et al., "Combination of Compressed Sensing and Parallel Imaging for Highly Accelerated First-Pass Cardiac Perfusion MRI", Magnetic Resonance in Medicine 64:767-776 (2010).

* cited by examiner

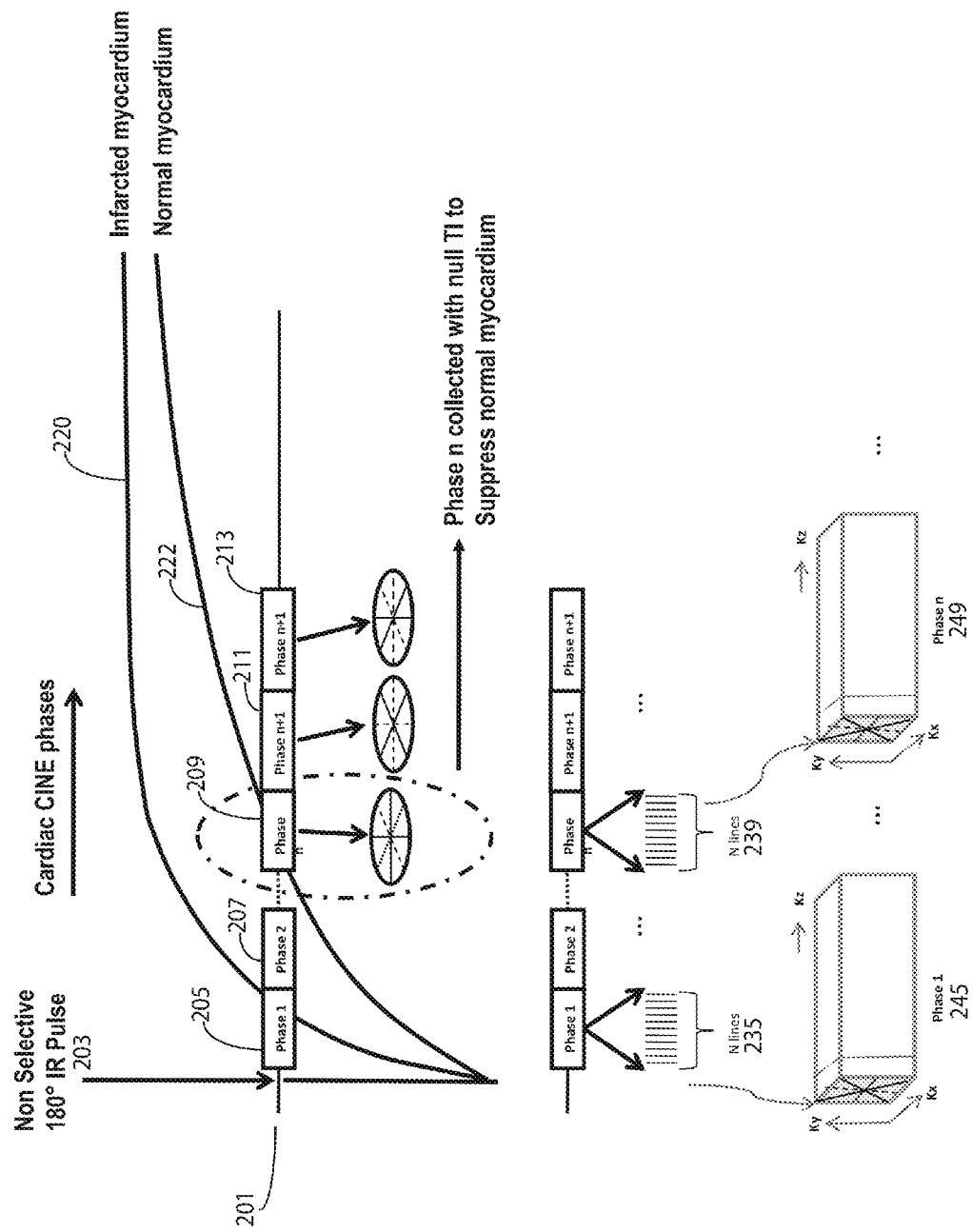

SYSTEM FOR CARDIAC MR AND MR CINE IMAGING USING PARALLEL IMAGE PROCESSING

This is a non-provisional application of provisional application Ser. No. 61/557,645 filed 9 Nov. 2011, by J. Xu.

FIELD OF THE INVENTION

This invention concerns a system for cardiac MR imaging using parallel image processing for generating MR images of individual heart cycle portions using multiple heart image representative data sets comprising a reduced set of k-space data elements in response to an RF inversion recovery pulse.

BACKGROUND OF THE INVENTION

Infarcted myocardium exhibits late gadolinium hyperenhancement (LGE) and is usually imaged with an inversion recovery (IR) sequence. The inversion time (TI) is typically set to null normal myocardial signal in order to maximize luminance contrast between normal and infarcted myocardium. A multi-slice multi-planar 2D (two dimensional) approach requiring multiple breath-holds (BH) is commonly used in routine clinical practice. An additional BH TI scout is utilized to determine the precise null time of normal myocardium in individual patients. The TI that is chosen and subsequently applied may not adequately null normal myocardium as 2D multi BH imaging proceeds over several minutes, due to gadolinium washout kinetics. Phase-sensitive inversion recovery (PSIR) imaging minimizes the need to precisely null normal myocardium, but as it requires two ECG signal RR wave peaks per trigger, BH 3D PSIR LGE imaging is challenging to perform. Highly accelerated 3D LGE enables acquisition of data at the same time point of contrast kinetics, which helps provide uniform suppression of the volume of normal myocardium within the imaged volume. However, this method still requires a TI scout and demonstrates relatively low signal noise ratio (SNR) compared to 2D methods due to the high acceleration factor and IR pulse used. Moreover, isotropic data is desired. A system according to invention principles addresses these deficiencies and needs and related problems.

SUMMARY OF THE INVENTION

A system improves temporal and spatial image resolution compared to known 3D (three dimensional) LGE methods by whole heart dynamic LGE imaging utilizing different TIs at different phases throughout a cardiac cycle within a single breath hold. A system for cardiac MR imaging uses parallel image processing. An input processor receives a heart rate signal representing heart electrical activity. Multiple MR imaging RF coils individually receive patient heart image representative data sets. An MR image acquisition system, over multiple successive heart cycles, uses multiple MR imaging RF coils in gradient echo imaging a patient heart, synchronized with the heart rate signal and uses an inversion recovery pulse for inverting myocardium tissue MR signal for an individual heart cycle, to acquire, within multiple individual successive portions of an individual heart cycle, corresponding successive multiple patient heart images. An individual image of an individual heart cycle portion is derived from multiple heart image representative data sets comprising a reduced set of k-space data elements acquired using corresponding multiple coils of the RF imaging coils. An image generator generates an MR image of an individual heart cycle portion using the multiple heart image representative data sets comprising the reduced set of k-space data elements.

BRIEF DESCRIPTION OF THE DRAWING

FIG. 2 shows a 4D cine pulse sequence using radial k-space acquisitions and parallel imaging, according to invention principles.

DETAILED DESCRIPTION OF THE INVENTION

A system according to invention principles in one embodiment employs radial acquisition and a k-t SPARSE sensitivity encoding (SENSE) reconstruction (k-t RASPS) method that results in improved temporal and spatial resolution compared to known 3D LGE methods. The system performs whole heart dynamic 4D LGE imaging utilizing different TIs at different phases throughout an entire cardiac cycle within a single breath hold using 4D stack-of-star radial acquisition and k-t RASPS. This is performed without the use of a TI scout acquisition to acquire image data for determining a time at which an MR signal from normal myocardium is nulled.

Figure 1:
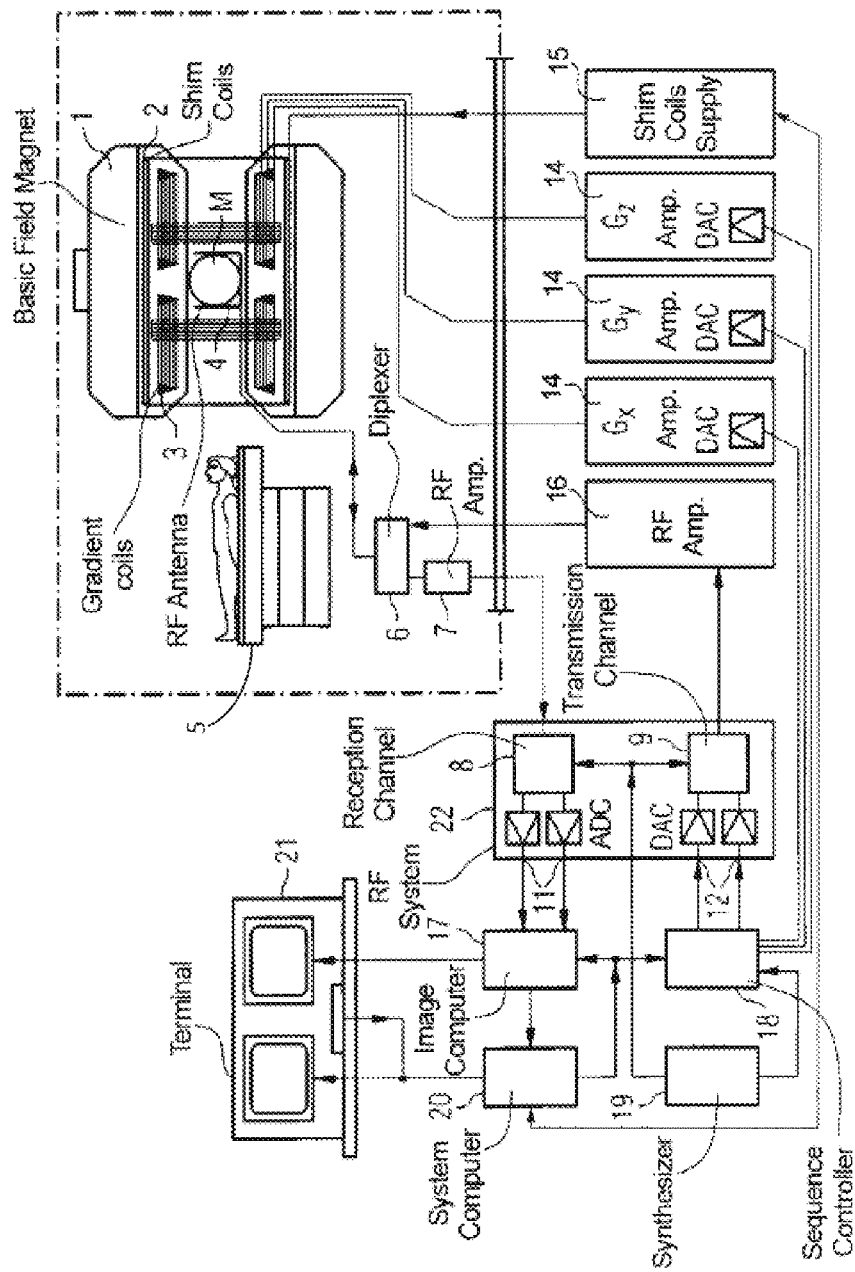
FIG. 1 shows a system for cardiac MR imaging using parallel image processing, according to invention principles.

FIG. 1 shows a schematic block diagram of MR imaging system 10 for cardiac MR imaging using parallel image processing. A basic field magnet 1 generates a strong magnetic field, which is constant in time, for the polarization or alignment of the nuclear spins in the examination region of an object, such as, for example, a part of a human body to be examined on patient support table 5. The high homogeneity of the basic magnetic field required for the magnetic resonance measurement is provided in a spherical measurement volume M, for example, into which the parts of the human body to be examined are brought. In order to satisfy the homogeneity requirements and especially for the elimination of time-invariant influences, shim-plates made of ferromagnetic material are mounted at suitable positions. Time-variable influences are eliminated by shim coils 2, which are controlled by a shim-current supply 15.

Imaging computer 17 reconstructs an image from processed acquired RF echo pulse data. The processing of RF data, the image data and the control programs is performed under control of system computer 20. In response to predetermined pulse sequence control programs, sequence controller 18 controls generation of desired pulse sequences and corresponding scanning of k-space. In particular, sequence controller 18 controls the switching of the magnetic gradients at appropriate times, transmission of RF pulses with a determined phase and amplitude and reception of magnetic resonance signals in the form of RF echo data. Synthesizer 19 determines timing of operations of RF system 22 and sequence controller 18. The selection of appropriate control programs for generating an MR image and the display of the generated nuclear spin image is performed by a user via terminal (console) 21, which contains a keyboard and one or more screens.

An input processor in imaging computer 17 receives a heart rate signal representing heart electrical activity. MR imaging RF coils 4 individually receive patient heart image representative data sets. MR imaging system 10, over multiple successive heart cycles, in conjunction with RF coils 4 performs gradient echo imaging of a patient heart, synchronized with the heart rate signal and uses an inversion recovery pulse for inverting myocardium tissue MR signal for each individual heart cycle. MR imaging system 10 uses RF coils 4 to acquire, within multiple individual successive portions of an individual heart cycle, corresponding successive multiple patient heart images. An individual image of an individual heart cycle portion is derived from multiple heart image representative data sets comprising a reduced set of k-space data elements acquired using corresponding multiple RF imaging coils. An image generator in computer 17 generates an MR image of an individual heart cycle portion using the multiple heart image representative data sets comprising the reduced set of k-space data elements.

FIG. 2 shows a 4D cine pulse sequence using radial k-space acquisitions and parallel imaging. MR imaging system 10 (FIG. 1) performs gradient echo imaging of a patient heart, over multiple successive heart cycles, using multiple RF coils 4. System 10 employs an imaging acquisition sequence 201 synchronized with a heart rate signal. Specifically, sequence 201 comprises a nonselective 180° inversion recovery pulse 203 used to improve T1 contrast by inverting normal myocardium tissue MR signal 222 for each individual heart cycle and synchronized with a heart cycle. Further, infarcted myocardium MR signal amplitude 220 for each individual heart cycle is nulled and near zero at a first time (an optimal TI) within a heart signal (phase 1) whereas normal myocardium tissue MR signal amplitude 222 is nulled at a different second time within the heart cycle (phase n). Magnetization MR signal amplitude for infarcted myocardium 220 and normal MR signal amplitude myocardium 222 is a function of delay time interval from inversion pulse 203. MR imaging system 10 performs k-space radial trajectory MR data signal sampling rotated through CINE cardiac phases 1 to n+1, for example. Imaging computer 17 reconstructs an image with typical luminance contrast for its phase for each phase (205, 207 . . . 209, 211, 213) having corresponding delay time interval from inversion recovery pulse 203. An individual phase comprises acquisition of multiple k-space data elements (eg k-space lines). In one embodiment, phase 1 (205) comprises acquisition of N k-space lines 235 of kx, ky data elements 245 over a time interval (kz dimension). Similarly, phase n (209) comprises acquisition of N k-space lines 239 of kx, ky data elements 249 over a time interval (kz dimension).

The MR image acquisition controller uses RF coils 4 to acquire, within multiple individual successive portions of an individual heart cycle comprising phases (205, 207 . . . 209, 211, 213), corresponding successive multiple patient heart images. An image is acquired for each phase. An individual image of an individual heart cycle portion is derived from multiple heart image representative data sets comprising a reduced set of k-space data elements (e.g. N lines 235) acquired using corresponding multiple RF imaging coils. An image generator in computer 17 generates an MR image of an individual heart cycle portion using the multiple heart image representative data sets comprising the reduced set of k-space data elements.

System 10 (FIG. 1) employs an ECG gated and substantially under-sampled 4D radial CINE Steady State Free Precession (SSFP) imaging sequence 201 (FIG. 2) with in-plane radial k-space sampling and through-plane Cartesian encoding. Non-selected inversion recovery pulse 203 is performed at the beginning of imaging sequence 201 to increase the T1 contrast between normal and infarcted myocardium. Single shot imaging of 10 spokes per slice radial k-space sampling is continuously performed to acquire image data in the cardiac phases (205, 207 . . . 209, 211, 213) of a heart cycle with the following imaging parameters, TR/TE 2.2/1.1 ms, readout 128, views 200, FOV (field of view) 360×360 mm2, slice number 40, slice partial Fourier 6/8, bandwidth 1502 Hz/pixel, 10 spokes per cardiac phase, temporal resolution 22 ms, spatial resolution 2.8×2.8×2.8 mm3. In single shot imaging, a raw data set used for generating at least one image, is acquired with a single RF excitation pulse. The total number of cardiac phases is dependent on heart rate (average 36 phases per cycle). K-t RASPS reconstruction is performed off-line with a Matlab (Mathworks, MA) derived application using a non linear conjugate gradient method and sparsifying transform. The parameters used in 3D late gadolinium hyper-enhancement (LGE) are, an IR prepared 3D SSFP sequence acquiring images during mid-diastole with GRAPPA factor 4 (PE)×2(3D), TR/TE 3.0/1.5 ms, matrix 144×144, number of slices 20 with thickness 6 mm, FOV (field of view) 360×360 mm2, spatial resolution 2.4×2.4×6 mm3, bandwidth 500 Hz/pixel. In order to determine the precise null time of normal myocardium, an additional TI scout was utilized for 3D LGE for comparison with a system performed method.

In an implementation MRI examinations are performed on a whole-body 1.5 Tesla scanner (MAGNETOM Avanto, Siemens, Erlangen, Germany) equipped with a high performance gradient system (maximum amplitude, 40 mT/m, maximum slew rate: 200 mT/m/ms) and a 32-element cardiac coil array. A contrast agent comprising Gd-DTPA 0.15 mmol/kg was administered. Two healthy patients (2 male, mean age 27) and a patient with a suspected cardiac condition (1 male, mean age 39) with suspected cardiomyopathy were examined using 4D and 3D LGE approximately 10-15 minutes after contrast agent administration.

Figures 3A, 3B:
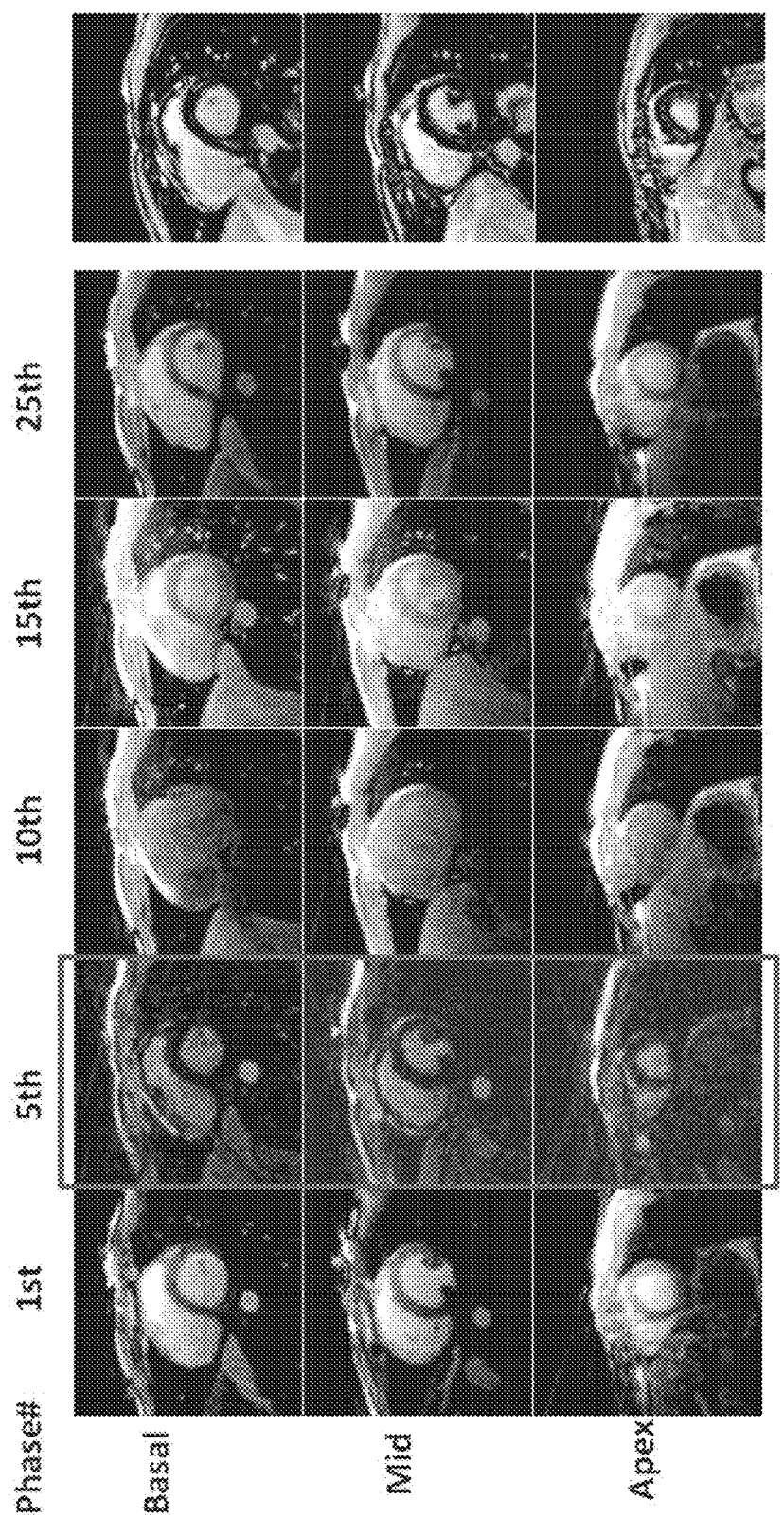
FIG. 3A shows MR images obtained in a 22-year-old healthy subject (160 lb, Male) without suspected cardiomyopathy showing different image luminance for different tissues with different T1s, according to invention principles.
FIG. 3B shows MR images corresponding to those of FIG. 3A and acquired using a 3D method and accelerated parallel imaging.

FIG. 3A shows MR images obtained by system 10 (FIG. 1) of a 22-year-old healthy subject (160 lb, Male) without suspected cardiomyopathy showing different image luminance for different tissues with different T1s. Base, mid and apical left ventricle selected short axis image slices (of 40 total slices) are shown in three rows for $1^{st}$, $5^{th}$, $10^{th}$, $15^{th}$ and $25^{th}$ heart cycle phases in corresponding individual columns A heart cycle includes 40 different total image phases with images acquired using 4D LGE imaging. The images show reasonable image quality results comprising isotropic data with whole heart coverage. Each row shows images in the same slice position but with different TI values from different cardiac phases. The images illustrate the TI dependence of image luminance contrast of different tissues with different T1s. In this example of 4D LGE, the 5th phase demonstrates an optimal phase with regard to nulling of normal myocardium. Dynamic motion of myocardium at different phases is depicted with phase 1 acquired during early systole, phase 5 acquired during systole and phase 25 acquired during mid-diastole.

FIG. 3B shows MR images corresponding to those of FIG. 3A and acquired using a known 3D method and accelerated parallel imaging. The corresponding base, mid and apical left ventricle selected short axis image slices of the three rows of FIG. 3B are acquired using 3D LGE imaging employing GRAPPA (Generalized autocalibrating partially parallel acquisition) reconstruction. The images are acquired during mid-diastole utilizing an additional TI scout acquisition to determine a precise null time of normal myocardium.

Figure 4:
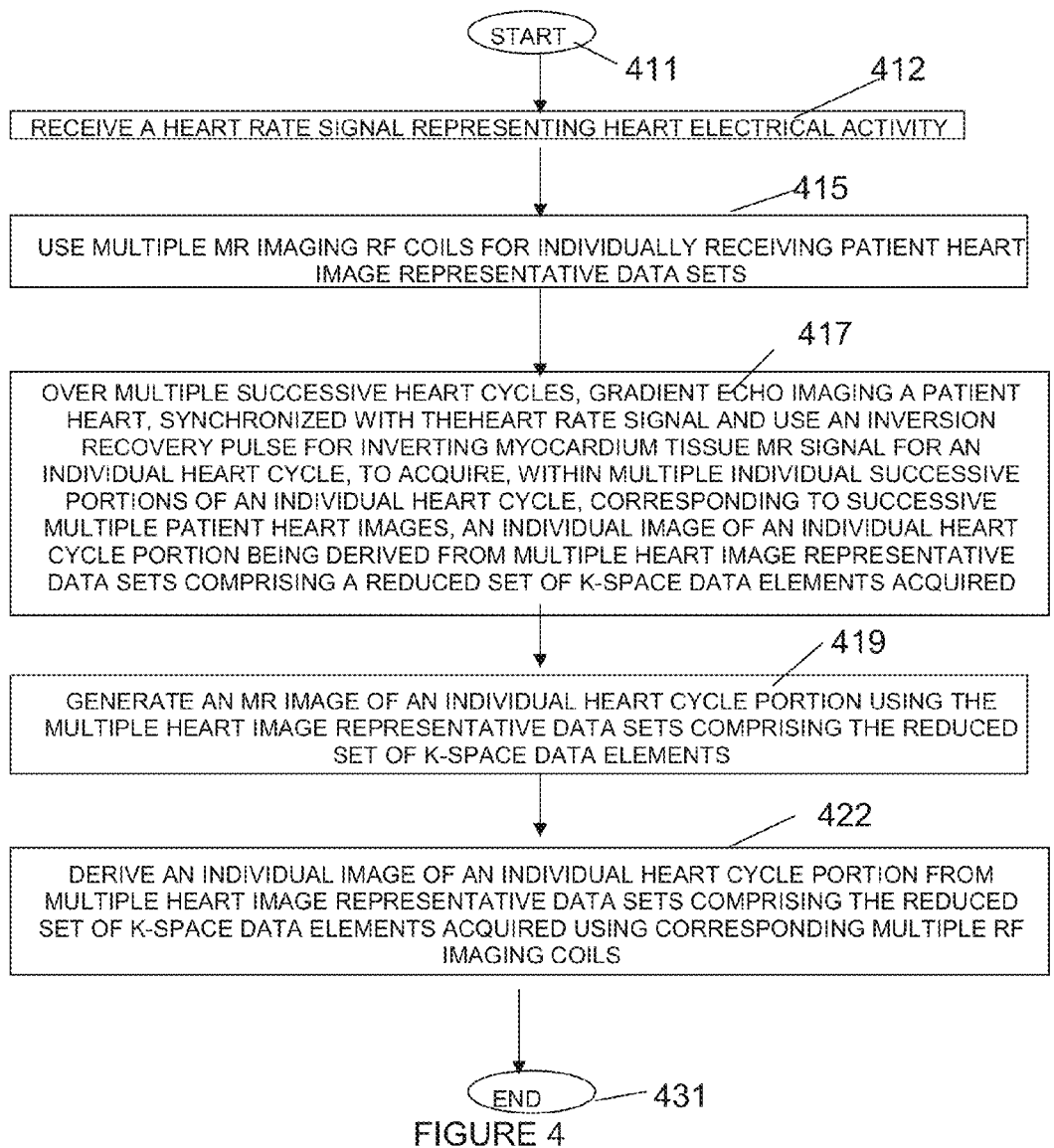
FIG. 4 shows a flowchart of a process performed by a system for Non-Contrast Agent enhanced MR imaging, according to invention principles.

FIG. 4 shows a flowchart of a process performed by a system for Non-Contrast Agent enhanced MR imaging. The system advantageously provides multiple TI-whole heart inversion recovery LGE imaging (4D LGE) with good nulling of normal myocardium within a breath-hold without the need for a TI scout. Relatively high temporal resolution and spatial resolution are advantageously achieved with the combination of radial sampling, parallel imaging and compressed sensing reconstruction. An approximate trigger delay and reduced phase number are used for image acquisition during diastole. In step 412 following the start at step 411, an input processor in imaging computer 17 receives a heart rate signal representing heart electrical activity. MR imaging RF coils 4 in step 415 individually receives patient heart image representative data sets.

In step 417 MR image acquisition system 10, over multiple successive heart cycles, uses the multiple MR imaging RF coils 4 in gradient echo imaging a patient heart, synchronized with the heart rate signal and uses an inversion recovery pulse for inverting myocardium tissue MR signal for an individual heart cycle, to acquire, within multiple individual successive portions of an individual heart cycle, corresponding successive multiple patient heart images. An individual image of an individual heart cycle portion is derived from multiple heart image representative data sets comprising a reduced set of k-space data elements acquired using corresponding multiple coils of RF imaging coils 4.

In step 419, an image generator in computer 17 generates an MR image of an individual heart cycle portion using the multiple heart image representative data sets comprising the reduced set of k-space data elements. The image generator generates the MR image of the individual heart cycle portion using the multiple heart image representative data sets comprising the reduced set of k-space data elements using a Sensitivity Encoding for Fast MRI (SENSE) method. The SENSE method generates the MR image of the individual heart cycle portion by reducing scan time using spatial information in image datasets acquired by the multiple MR imaging RF coils for reducing Fourier encoding. In one embodiment, the image generator generates the MR image of the individual heart cycle portion using the multiple heart image representative data sets comprising the reduced set of k-space data elements using a combined sparse SENSE reconstruction method. Further, the image generator generates the MR image of the individual heart cycle portion using the multiple heart image representative data sets comprising the reduced set of k-space data elements on a radial k-space trajectory.

In step 422 the image generator derives an individual image of an individual heart cycle portion from multiple heart image representative data sets comprising the reduced set of k-space data elements acquired using corresponding multiple RF imaging coils. The MR image acquisition system uses the multiple MR imaging RF coils to acquire a video clip of the patient heart comprising the multiple patient heart images in the multiple successive heart cycles. Also the system acquires the corresponding successive multiple patient heart images exclusive of use of a scout image acquisition to determine a null time of normal myocardium. The process of FIG. 4 terminates at step 431.

Returning to FIG. 1, in the basic magnetic field 1, a cylinder-shaped gradient coil system 3 is used, which consists of three windings, for example. Each winding is supplied with current by an amplifier 14 in order to generate a linear gradient field in the respective directions of the Cartesian coordinate system. The first winding of the gradient field system 3 generates a gradient $G_x$ in the x-direction, the second winding generates a gradient $G_y$ in the y-direction, and the third winding generates a gradient $G_z$ in the z-direction. Each amplifier 14 contains a digital-analog converter, which is controlled by a sequence controller 18 for the generation of gradient pulses at proper times.

Within the gradient field system 3, radio-frequency (RF) coils 4 are located which converts the radio-frequency pulses emitted by a radio-frequency power amplifier 16 via multiplexer 6 into a magnetic alternating field in order to excite the nuclei and align the nuclear spins of the object to be examined or the region of the object to be examined. In one embodiment, RF coils 4 comprise a subset or substantially all of, multiple RF coils arranged in sections along the length of volume M corresponding to the length of a patient. Further, an individual section RF coil of coils 4 comprises multiple RF coils providing RF image data that is used in parallel to generate a single MR image. RF pulse signals are applied to RF coils 4, which in response produces magnetic field pulses which rotate the spins of the protons in the imaged body by ninety degrees or by one hundred and eighty degrees for so-called "spin echo" imaging, or by angles less than or equal to 90 degrees for so-called "gradient echo" imaging. In response to the applied RF pulse signals, RF coils 4 receive MR signals, i.e., signals from the excited protons within the body as they return to an equilibrium position established by the static and gradient magnetic fields. The MR signals comprising nuclear spin echo signals received by RF coils 4 as an alternating field resulting from the precessing nuclear spins, are converted into a voltage that is supplied via an amplifier 7 and multiplexer 6 to a radio-frequency receiver processing unit 8 of a radio-frequency system 22.

The radio-frequency system 22 operates in an RF signal transmission mode to excite protons and in a receiving mode to process resulting RF echo signals. In transmission mode, system 22 transmits RF pulses via transmission channel 9 to initiate nuclear magnetic resonance in volume M. Specifically, system 22 processes respective RF echo pulses associated with a pulse sequence used by system computer 20 in conjunction with sequence controller 18 to provide a digitally represented numerical sequence of complex numbers. This numerical sequence is supplied as real and imaginary parts via digital-analog converter 12 in the high-frequency system 22 and from there to a transmission channel 9. In the transmission channel 9, the pulse sequences are modulated with a radio-frequency carrier signal, having a base frequency corresponding to the resonance frequency of the nuclear spins in the measurement volume M. The conversion from transmitting to receiving operation is done via a multiplexer 6. RF coils 4 emit RF pulses to excite nuclear proton spins in measurement volume M and acquire resultant RF echo signals. The correspondingly obtained magnetic resonance signals are demodulated in receiver processing unit 8 of RF system 22 in a phase-sensitive manner, and are converted via respective analog-digital converters 11 into a real part and an imaginary part of the measurement signal and processed by imaging computer 17.

DEFINITIONS 4D comprises four dimensional, 3 spatial dimensions over a time dimension.

A single imaging scan comprises an automated image acquisition process for acquiring a sequence of images using an imaging system that is performed according to predetermined instruction and without human intervention.

An inversion recovery (IR) pulse inverts longitudinal magnetization from the positive z-axis by 180 degrees to the negative z-axis. IR pulses are used as preparation pulses prior to a main imaging pulse sequence to achieve different kinds of MR contrast (such as T1 weighted, T2 weighted). Adiabatic IR pulses are used to give more uniform contrast throughout an imaging volume than non-adiabatic RF pulses.

iPAT (integrated Parallel Acquisition Techniques) comprises "parallel imaging". It enables faster scanning through reduced phase encoding and addition of RF coil information. An iPAT factor of 2 enables scanning about twice as fast, iPAT factor of 3 enables scanning about three times as fast and so on.

TI comprises inversion time, the time between an inversion recovery pulse and the next RF excitation pulse. TI determines the image contrast.

$T_1$ comprises the longitudinal (or spin-lattice) relaxation time $T_1$ decay constant.

$T_2$ comprises the transverse (or spin-spin) relaxation time $T_2$ is the decay constant for a proton spin component.

TR comprises repetition time, the time between successive RF excitation pulses.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication there-between. Computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s). A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-4 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. An MR system uses multiple RF coils to provide a 4D cine pulse sequence using parallel imaging over multiple successive heart cycles synchronized with a heart rate signal and uses a nonselective 180° inversion recovery pulse to improve T1 contrast by inverting normal myocardium tissue MR signal for each individual heart cycle. Further, the processes and applications may, in alternative embodiments, be located on one or more (e.g., distributed) processing devices on a network linking the units of FIG. 1. Any of the functions and steps provided in FIGS. 1-4 may be implemented in hardware, software or a combination of both. No claim element herein is to be construed under the provisions of 35 U.S.C. 112, sixth paragraph, unless the element is expressly recited using the phrase "means for."

What is claimed is:

1. A method for cardiac imaging that nulls a normal myocardium signal without use of a scout, the method comprising:

for each of a plurality of cardiac cycles within a single breath hold:

applying a non-selective inversion pulse during the cardiac cycle;

identifying a plurality of successive phases of the cardiac cycle that are immediately subsequent to the non-selective inversion pulse, wherein there is no intervening time between application of the non-selective inversion pulse and the start of the plurality of successive phases of the cardiac cycle; and performing single shot imaging to sample MR data along radial trajectories in k-space continuously during each of the successive phases of the cardiac cycle using a plurality of MR imaging RF coils to simultaneously acquire a plurality of reduced sets of k-space data elements associated with each of the successive phases of the cardiac cycle;

performing k-t SPARSE-SENSE reconstruction on the plurality of reduced sets of k-space data elements acquired during corresponding phases of different ones of the plurality of cardiac cycles to generate an image for each of the phases of the cardiac cycle; and selecting one image of the plurality of images generated for the plurality of phases of the cardiac cycle in which the normal myocardium signal is nulled, wherein the MR data comprises gradient echo imaging data; and wherein the corresponding phases of different ones of the plurality of cardiac cycles have a same delay time interval from the non-selective inversion recovery pulse.

2. The method of claim 1, further comprising:
receiving a plurality of heart rate signals associated with heart electrical activity of the cardiac cycle in the patient; and
identifying the plurality of successive phases of each of the cardiac cycles based on the heart rate signals.

3. The method of claim 1, wherein the number of phases of the cardiac cycle is 36.

4. The method of claim 1, wherein each of the reduced sets of k-space data elements associated with each of the successive phases of the cardiac cycle comprises a plurality of in-plane radial spokes in k-space obtained in each of a plurality of slices using through-plane Cartesian encoding.

5. The method of claim 1, wherein the k-t SPARSE-SENSE reconstruction generates each image based on a reduced scan time by using spatial information acquired by the plurality of RF imaging coils for reducing Fourier encoding.

6. The method of claim 1, wherein a time interval between the non-selective inversion pulse of the cardiac cycle and a first phase of the plurality of successive phases of the cardiac cycle is selected such that an MR signal amplitude for infracted myocardium is nulled within the first phase.

7. The method of claim 1, further comprising:
associating a particular inversion time that corresponds to a time interval between the non-selective inversion pulse and the one image of the plurality of images generated for the plurality of phases of the cardiac cycle in which the normal myocardium signal is nulled; and
identifying a null time of normal myocardium without use of an inversion time scout as the particular inversion time.

8. The method of claim 1, further comprising:
generating a video clip of the cardiac cycle based on the image generated for each of the phases of the cardiac cycle.

9. A system for cardiac imaging that nulls a normal myocardium signal without use of a scout, the system comprising:
an MR imaging system configured to:
apply a non-selective inversion pulse during each cardiac cycle of a plurality of cardiac cycles within a single breath hold;
identify successive phases of each cardiac cycle that are immediately subsequent to the non-selective inversion pulse, wherein there is no intervening time between the application of the non-selective inversion pulse and the start of the successive phases of the cardiac cycle; and
perform single shot imaging to sample MR data along radial trajectories in k-space continuously during each of the successive phases of each the cardiac cycle to acquire a plurality of k-space data elements associated with each of the successive phases of the cardiac cycle; and
a computer configured to:
perform k-t SPARSE-SENSE reconstruction on the plurality of k-space data elements acquired during corresponding phases of different ones of the plurality of cardiac cycles to generate an image for each of the phases of the cardiac cycle,
wherein the MR data comprises gradient echo imaging data; and
wherein the corresponding phases of different ones of the plurality of cardiac cycles have a same delay time interval from the non-selective inversion recovery pulse.

10. The system of claim 9, further comprising:
an input processor configured to:
receive a plurality of heart rate signals associated with heart electrical activity of the cardiac cycle in the patient; and
identify the plurality of successive phases of each cardiac cycle based on the heart rate signals.

11. The system of claim 9, wherein the number of phases of the cardiac cycle is 36.

12. The system of claim 9, wherein the MR imaging system comprises a plurality of MR imaging RF coils configured to sample the MR data and simultaneously acquire reduced sets of k-space data elements included in the plurality of k-space data elements.

13. The system of claim 12, wherein the plurality of k-space data elements associated with each of the successive phases of the cardiac cycle comprises a plurality of in-plane radial spokes in k-space obtained in each of a plurality of slices using through-plane Cartesian encoding.

14. The system of claim 9, wherein the system is further configured to select a time interval between the non-selective inversion pulse of each cardiac cycle and a first phase of the plurality of successive phases of the cardiac cycle such that an MR signal amplitude for infracted myocardium is nulled within the first phase.

15. The system of claim 9, wherein the system is further configured to:
associate a particular inversion time that corresponds to a time interval between the non-selective inversion pulse and the one image of the plurality of images generated for the plurality of phases of the cardiac cycle in which the normal myocardium signal is nulled; and
identify a null time of normal myocardium without use of an inversion time scout as the particular inversion time.

16. The system of claim 9, wherein the computer is further configured to generating a video clip of the cardiac cycle based on the image generated for each of the phases of the cardiac cycle.

* * * * *